United States Patent
Trovato

(10) Patent No.: US 9,387,047 B2
(45) Date of Patent: Jul. 12, 2016

(54) INTERSTITAL LUNG ACCESS USING NESTED CANNULAS

(71) Applicant: KONINKLIJKE PHILIPS N.V., Eindhoven (NL)

(72) Inventor: Karen Irene Trovato, Putnam Valley, NY (US)

(73) Assignee: Koninklijke Philips N.V., Eindhoven (NL)

( * ) Notice: Subject to any disclaimer, the term of this patent is extended or adjusted under 35 U.S.C. 154(b) by 59 days.

(21) Appl. No.: 14/361,141

(22) PCT Filed: Nov. 27, 2012

(86) PCT No.: PCT/IB2012/056756
§ 371 (c)(1),
(2) Date: May 28, 2014

(87) PCT Pub. No.: WO2013/080123
PCT Pub. Date: Jun. 6, 2013

(65) Prior Publication Data
US 2015/0012011 A1    Jan. 8, 2015

Related U.S. Application Data

(60) Provisional application No. 61/566,613, filed on Dec. 3, 2011.

(51) Int. Cl.
*G06K 9/00* (2006.01)
*A61B 19/00* (2006.01)
(Continued)

(52) U.S. Cl.
CPC ............. *A61B 19/50* (2013.01); *A61B 17/3421* (2013.01); *G06T 7/0012* (2013.01); *G06T 19/003* (2013.01); *A61B 2017/00331* (2013.01); *A61B 2017/00991* (2013.01);
(Continued)

(58) Field of Classification Search
None
See application file for complete search history.

(56) References Cited

U.S. PATENT DOCUMENTS

2011/0092810 A1* 4/2011 Trovato .............. A61B 17/3421
600/424
2011/0245625 A1* 10/2011 Trovato .............. A61B 17/3421
600/300

FOREIGN PATENT DOCUMENTS

WO    WO2009156892    12/2009

OTHER PUBLICATIONS

Trovato, Karen, and Aleksandra Popovic. "Collision-free 6D non-holonomic planning for nested cannulas." SPIE Medical Imaging. International Society for Optics and Photonics, 2009.*

*Primary Examiner* — Shefali Goradia

(57) ABSTRACT

A cannula configuration method involves a generation of a discretized configuration space of a three dimensional image of an anatomical region, the discretized configuration space including a free-space for navigation of a nested cannula within the anatomical region and a forbidden space unreachable by the nested cannula. The method further involves a selection of a tube target location (24) within the free-space, the tube target location (24) being derived from a computation of contiguous tool trajectory nodes of the discretized configuration space representative of a trajectory of a surgical tool extending through the nested cannula from the tube target location (24) within the free-space to a tool target location (23) within the forbidden space. The method further involves a generation of a series of concatenated path shapes between the tube entry location (24) and the tube target location to form a cannula configuration pathway within the free-space.

20 Claims, 7 Drawing Sheets

(51) Int. Cl.
*A61B 17/34* (2006.01)
*G06T 7/00* (2006.01)
*G06T 19/00* (2011.01)
*A61B 17/00* (2006.01)

(52) U.S. Cl.
CPC *A61B 2019/508* (2013.01); *G06T 2207/10081* (2013.01); *G06T 2207/30021* (2013.01); *G06T 2207/30061* (2013.01); *G06T 2207/30241* (2013.01)

INTERSTITAL LUNG ACCESS USING NESTED CANNULAS

CROSS-REFERENCE TO PRIOR APPLICATIONS

This application is the U.S. National Phase application under 35 U.S.C. §371 of International Application Serial No. PCT/IB2012/056756, filed on Nov. 27, 2012, which claims the benefit of U.S. Application Ser. No. 61/566,613, filed on Dec. 3, 2011. These applications are hereby incorporated by reference herein.

The present disclosure generally relates to medical procedures involving cannula, particularly minimally invasive surgical procedures. The present disclosure specifically relates to systems and methods related to cannula configurations for facilitating a surgical tool (e.g., a straight needle or a curved needle) reaching interstitial anatomical regions.

For purposes of the present invention, the term "nested cannula" refers to a device constructed with nested, lengthwise interlocking tubes, typically extended sequentially from largest to smallest. Applicant's prior, pending application entitled "Nested Cannulae for Minimally Invasive Surgery", International Publication No. WO 2009/156892, Nov. 10, 2010, which is incorporated, in its entirety, by reference herein and made a part of this specification, discloses systems and methods for a nested cannula configuration to reach a target location within a particular anatomical region depending upon the requirements of the medical procedure. In order to use a nested cannula by sequential deployment, the configuration of the tubes must be defined so that the path and the final pre-determined position of the distal tip may be achieved.

More particularly, nested cannulas are constructed based on a patient's three-dimensional ("3D") image to reach a particular target inside the patient. Each nested cannula is specifically built for each person, each approach-angle and each target. As related to bronchial trees, nested cannulas are constructed so that they stay within the airways, reaching suspicious areas that are along or within the airways.

For example, as taught by International Publication No. WO 2009/156892, special regions may be 'painted out', enabling free-space to extend along a path to a target. However, this technique presumes that the cannula pathway planner knows a valid, achievable route given a particular surgical tool, and that the 'painter' provides the complete additional free-space region required.

Additionally, most surgical tools are designed to stay within the permitted, or free-space of anatomy. However, it is not always possible to identify the finest anatomical details based on image segmentation, for example.

Furthermore, airways are usually a connected series of branches that become smaller as they split. Current imaging resolution and segmentation algorithms cannot yet resolve down to the tiniest alveoli, and in fact leave relatively large areas between the segmentable airways. Although these areas are un-segmented, lesions may be detected in these regions. The problem therefore is that no legal airway may lead directly to the lesion. If the cannula pathway planner must stay inside 'legal regions', then the surgical tool cannot reach the lesion.

A great deal of manual effort may be required if the approach orientation to the target is not easily fixed. For example, a tumor location may be identified, but numerous airways nearby, may provide many angle choices. This is further complicated if the tool has a curve or other non-linear shape, or if the region has many locations where the tool may cross out of free-space.

The present invention allows a cannula pathway planner to select a tube target location within the free-space to facilitate a surgical tool extending through a nested cannula to reach a tool target location within the previously labeled forbidden space.

One form of the present invention is a system employing an image discretization module, a target selection module and a cannula configuration module. In operation, the image discretization module generates a discretized configuration space of a three dimensional image of an anatomical region, the discretized configuration space including a free-space for navigation of a nested cannula within the anatomical region and a forbidden space unreachable by the nested cannula. The target selection module selects a tube target location within the free-space, the tube target location being derived from a computation of contiguous tool trajectory nodes of the discretized configuration space representative of a trajectory of a surgical tool extending through the nested cannula from the tube target location within the free-space to a tool target location within the forbidden space. The selection of the tube target location is a function of a heuristic cost metric of at least one tool trajectory node, each non-finite heuristic cost metric being indicative of an estimated distance from a corresponding tool trajectory node to a tube entry location in the free-space. The cannula pathway module generates a series of concatenated path shapes between the tube target location and a tube entry location (e.g., a patient's mouth or a patient's nose) to form a cannula configuration pathway within the free-space. The cannula configuration pathway serves as a specification for configuring and dimensioning the plurality of the concentric telescoping tubes to reach the tube target location from the tube entry location.

A second form of the present invention is a cannula system employing a nested cannula configured and dimensioned to extend from a tube entry location into a free-space of a discretized configuration space of a three dimensional image of an anatomical region to a tube target location within the free-space. The cannula system further employs a surgical tool configured and dimensioned to extend through the nested cannula from the tube target location to a tool target location within a forbidden space of the discretized configuration space. The configuration of the plurality of telescoping tubes is derived by computing contiguous tool trajectory nodes of the discretized configuration space representing a trajectory of the surgical tool from the tool target location through the forbidden space to the tube target location in free-space. The configuration of the plurality of telescoping tubes is further derived from a selection of the tube target location based on a-infinite heuristic cost metric of one or more of the tool trajectory nodes. Each heuristic cost represents an estimated distance from a corresponding tool trajectory node to the tube entry location.

A third form of the present invention is a cannula configuration method involves generating a discretized configuration space of a three dimensional image of an anatomical region, the discretized configuration space including a free-space for navigating a nested cannula within the anatomical region and a forbidden space unreachable by the nested cannula. The cannula configuration method further involves a selection of a tube target location within the free-space, the tube target location being derived by computing contiguous tool trajectory nodes of the discretized configuration space representative of a trajectory from a tool target location extending through forbidden space into free-space. The tube target location is selected based on a heuristic cost metric of one or more tool trajectory nodes. The cannula configuration method further involves a generation of a series of concatenated path shapes between the tube entry location and the tube target location to form a cannula configuration pathway within the free-space. The cannula configuration pathway serves as a specification for a configuration and dimensioning of the plurality of the concentric interlocking, telescoping tubes to reach tube the tube target location from the tube entry location.

The present invention provides nested cannula configuration systems and methods that generate a nested cannula customized to a patient and/or anatomical region-of-interest and/or anatomical structure in question. The disclosed systems and methods advantageously enable minimally invasive surgical procedures to reach particular target locations that are commonly difficult to reach by traditional surgical means.

Figure 1:
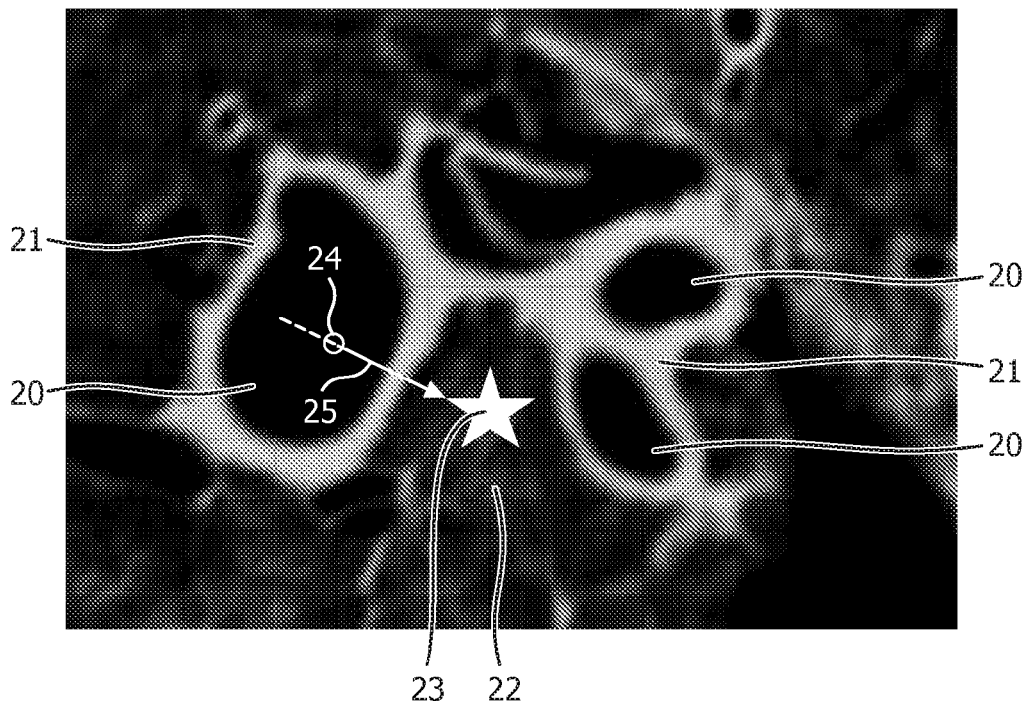
FIG. 1 illustrates a simulation of a trajectory of a surgical tool extending from a tube target location 24 to a tool target location 23 in accordance with the present invention.

Specifically, for example, FIG. 1 illustrates a two-dimensional ("2D") slice of a bronchial tree having airways 20 and an interstitial region 22 between airways 20. Airways 20 represent free-space within the bronchial tree for navigation of a nested cannula therein and interstitial region 22 represents forbidden space for the nested cannula. More particularly, as related to a discretized configuration space of the 2D slice of the bronchial tree, the airways have a non-infinite cost while the bronchial walls 21 and interstitial region 22 have a high (representing infinite) cost. Thus, the prior nested cannula techniques cannot be configured to reach a lesion within interstitial region 22. The present invention provides a technique for configuring the nested cannula (not shown) to reach a tube target location 24 from a tube entry location (not shown) into the bronchial tree and for an extension of a surgical tool 25 through the nested cannula from the tube target location 24 to a tool target location 23 corresponding to a lesion.

Figure 2:
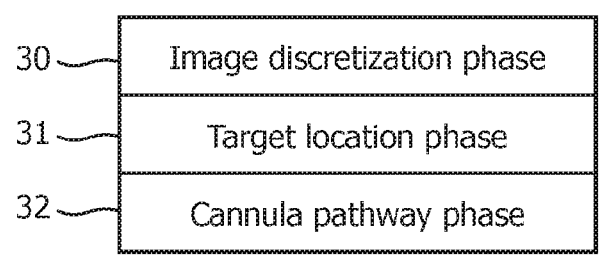
FIG. 2 illustrates is a block diagram of various phases of a cannula configuration method in accordance with the present invention.

In general, as shown in FIG. 2, the technique involves three (3) phases. An image discretization phase 30 involves a generation of a discretized configuration space of a 3D image of anatomical region including the free-space and the forbidden space. A target location phase 31 involves a selection of a tool target location corresponding to a lesion or any other particular area of interest within the forbidden space and a selection of a tube target location within the free-space for extending a surgical tool through the nested cannula to the tool target location. The final cannula pathway phase 32 involves a generation of a cannula configuration pathway between the tube target location and the tube entry location through the free-space whereby the pathway is used to configure and dimension the nested cannula.

Figure 3:
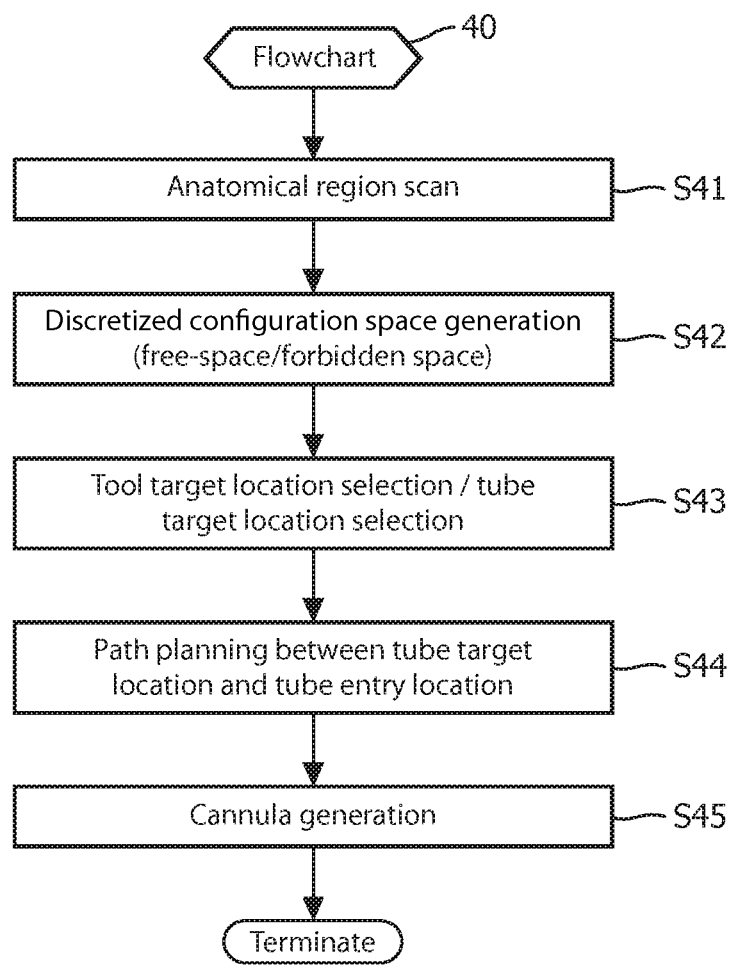
FIG. 3 illustrates a flowchart representative of one embodiment of the cannula configuration method shown in FIG. 2.

The following description of a cannula configuration method of the present invention as represented by a flowchart 40 shown in FIG. 3 facilitates a more detailed understanding of the various phases of FIG. 2.

Referring to FIG. 3, a stage S41 of flowchart 40 encompasses a 3D scan of an anatomical region as known in the art, such as, for example, a CT scan of a bronchial tree as shown in FIG. 1.

Figure 4:
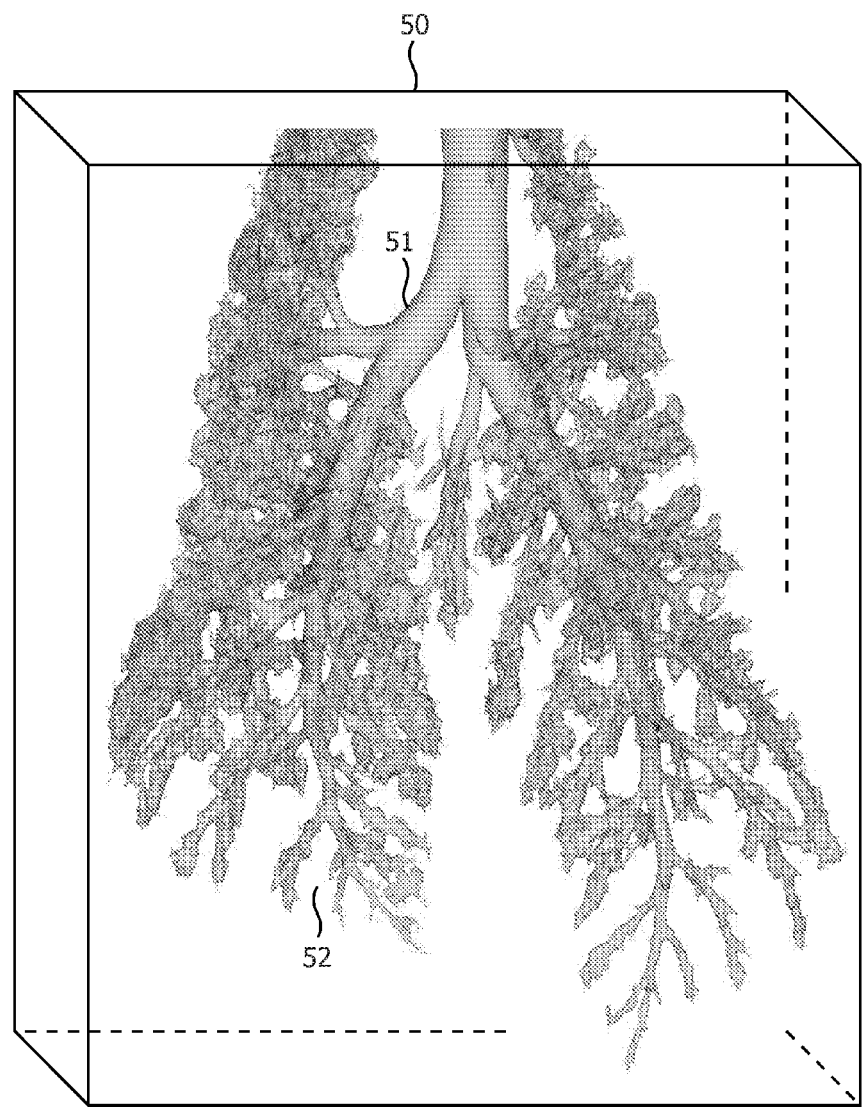
FIG. 4 illustrates an exemplary image scan and segmentation of a bronchial tree as known in the art.

A stage S42 of flowchart 40 encompasses a generation of a discretized configuration space of the 3D scan of the anatomical region. The discretized configuration space will include the free-space of the anatomical region, created by segmentation methods known in the art, and will further include forbidden space of the anatomical region. For example, the discretized configuration space 50 of FIG. 4 includes free-space airways 51 and an interstitial region 52 between airways 51.

A stage S43 of flowchart 40 encompasses a selection of the tool target location within the forbidden space and a selection of a tube target location within the free-space. A stage S44 of flowchart 40 encompasses a generation of a series of concatenated path shapes between the tube entry location and the tube target location to form a cannula configuration pathway within the free-space. As known in the art, the cannula configuration pathway serves as a specification for configuring and dimensioning the nested cannula to reach the tube target location from the tube entry location during a stage S45 of FIG. 3. A flowchart 60 shown in FIG. 5 represents one embodiment of stages S43 and S44.

Figure 5:
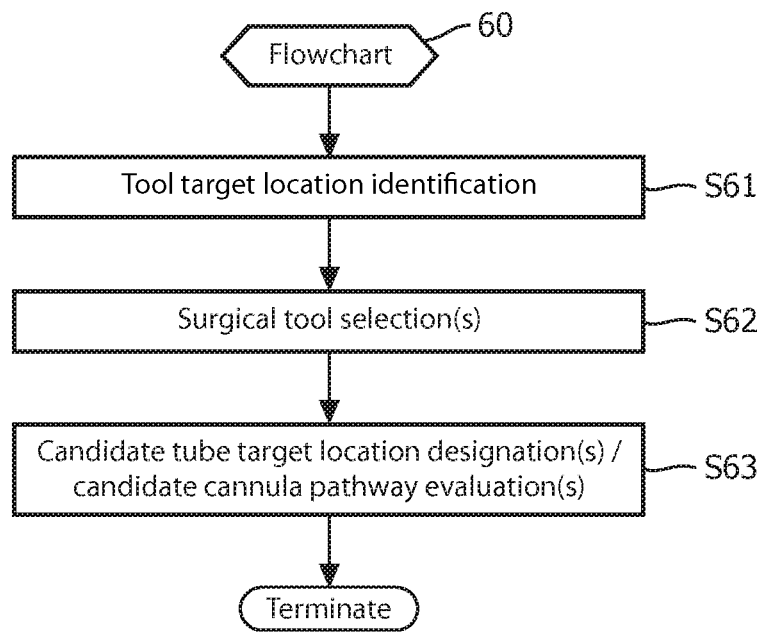
FIG. 5 illustrates a flowchart representative of a tube target location selection method in accordance with the present invention.
Figure 6:
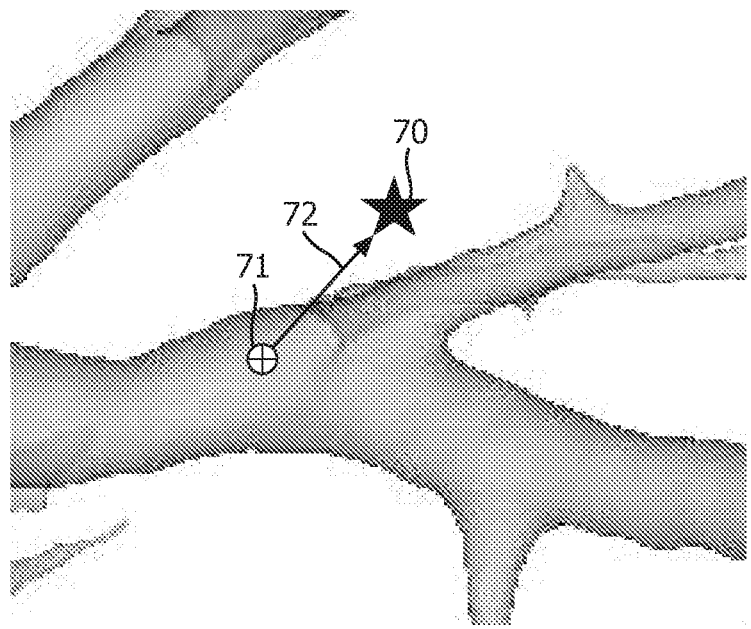
FIG. 6 illustrates an exemplary semi-automatic selection mode of candidate tube target location(s) in accordance with the present invention.

Referring to FIG. 5, a stage S61 of flowchart 60 encompasses an identification of the tool target location. In one embodiment, the image is reviewed by a radiologist on an imaging system (e.g., a Picture Archiving and Communication System) and a suspicious lesion may be detected and marked for example with a red star. For example as shown in FIG. 6, the radiologist may mark a red star at a tool target location 70 corresponding to a lesion in a forbidden interstitial region of a 3D scan of a bronchial tree. In an alternate embodiment, lesion detection may be performed by a Computer Aided Detection system to speed the process of identifying the most suspicious lesions and any detected lesion is marked as the tool target location.

A stage S62 of flowchart 60 encompasses a selection of one of a set of surgical tools to be utilized to reach the tool target location using the nested cannula. In one embodiment, a particular surgical tool is selected (e.g., a straight needle of a given length) for extension from the last cannula of the nested cannula to the tool target location. In an alternate embodiment as subsequently explained herein, two or more tools are compared so that the best tool, having the lowest overall cost, may be recommended.

A stage S63 of flowchart 60 encompasses a use of the selected tool or tools in designating one or more candidate tube target locations, and in evaluating candidate cannula pathways between the tube entry location and each candidate tube target location.

In one embodiment of stage S63, as shown in FIG. 6, a radiologist can set a desired tool trajectory by selecting a target area 71 within the free-space. A tool trajectory 72 becomes a direction of the arrow, such as, for example, if the selected tool is a straight biopsy needle. Each node of the tool trajectory is evaluated starting at the tool target location 70 or the end of the tool trajectory 72 within the airways until a viable free-space position is identified, along with the cost incurred, for example given as distance travelled. This is the equivalent of searching for free-space along the specified trajectory. In this case, the tool target location is at the tool tip.

A range of orientations from that point may be explored, wherein the orientation and rotation of the tool is stored as an option, along with the cost, at a free-space candidate tube target location. The best tool choice, is therefore the lowest total cost of all the options, where each cost is the sum of the cost incurred plus the heuristic (estimated cost to reach the entry). This lowest total cost option provides the location of the tube target (position and orientation), the proposed tool and the amount it extends, as well as the resulting tool target orientation (3D location is already selected).

For this embodiment, the evaluation will involve a search from a candidate tube target location, including the tube target orientation, to a tube entry location within the free-space. Free-space may be identified as having a non-infinite transition cost, however it is possible that segmentation techniques can create a free-space location that is not in fact reachable from the entry location. If a heuristic has been computed for all reachable nodes, the testing for a non-infinite heuristic cost may be used as an indication of free-space. The evaluation may be of a first node encountered along a tool trajectory 72 having a non-infinite heuristic cost, but within a given length, or else some fixed number of nodes along the trajectory may be options. Computed tube-set alternatives may be displayed for a selection of one candidate as the final tube target location or alternatively, the final tube target location may be automatically selected based on the fewest number of component tubes generated during the searches.

Figure 7:
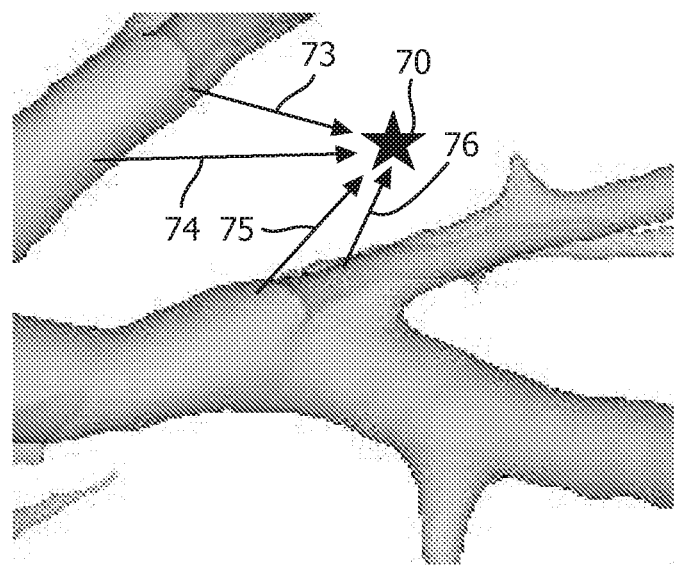
FIGS. 7-10 illustrate an exemplary automatic selection mode of candidate tube target location(s) in accordance with the present invention.

A second embodiment of stage S63 (FIG. 5) is shown in FIG. 7. A tool target location 70 may be identified where numerous airways lead nearby, thus providing many choices 73-76 for the tool trajectory orientation. In this embodiment, the orientation of the tool trajectory is defined independently of the length of the surgical tool.

Figure 8:
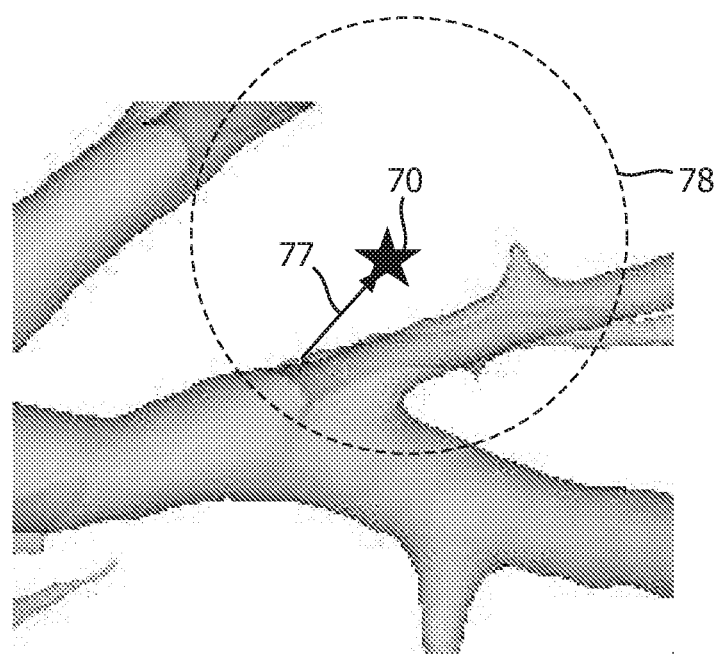

Specifically, as shown in FIG. 8, a boundary of a maximum tool-length 78 defines a maximum overall volume that may reach the tool target location. The nodes within this volume that are 'legal airways' are then possible nodes that may help set the approach angle(s) to the tool target location 70. The preferred nodes are those with the lower heuristic values, since they indicate the best direction leading toward the tube entry location (e.g. trachea) using legal airways.

Figure 9:
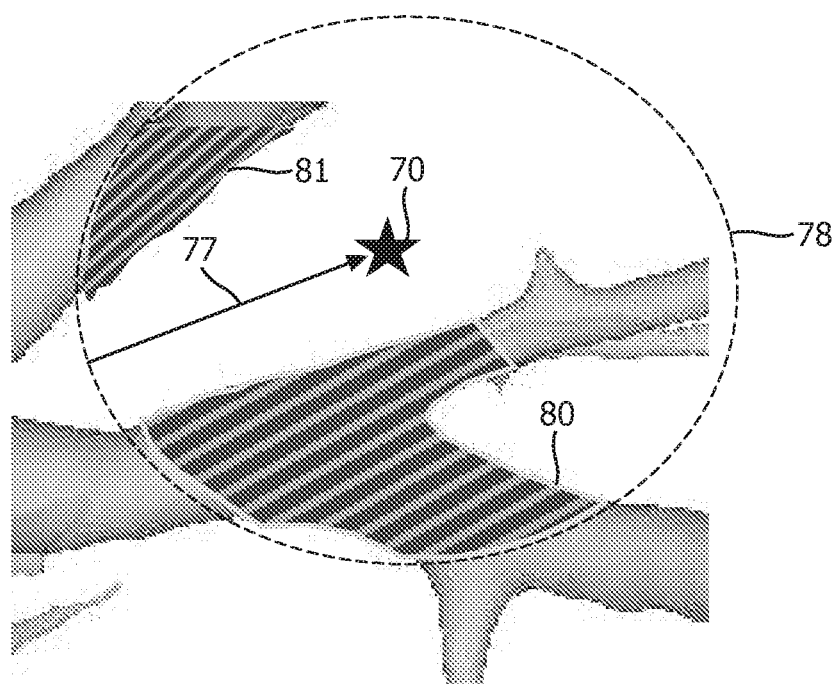
Figure 10:
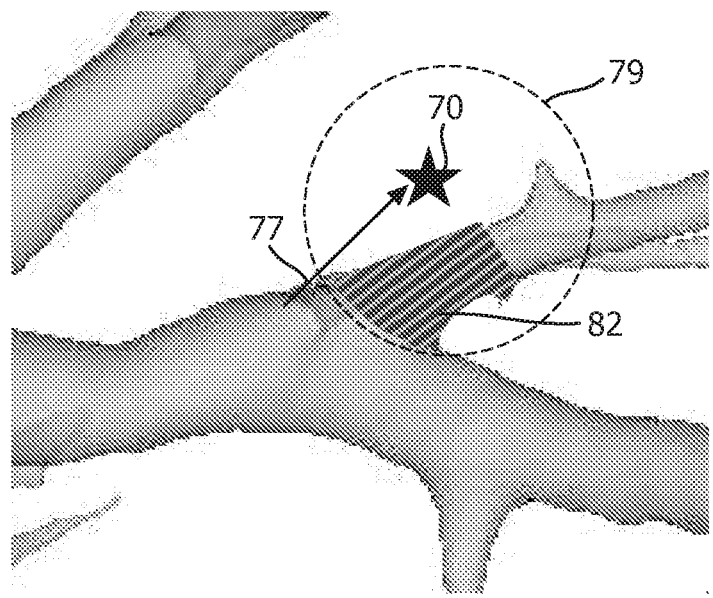

For example, a biopsy needle may be extended to the maximum length 77 as shown in FIG. 8. In this case, the 3D region required for assessment is within reach of the surgical tool, forming a sphere 78. There are heuristic values throughout the airway. The values may provide the 'distance yet to go' for example, therefore the lower values will be in the general direction of the tube entry location for example. Since their are so many available, the lower values are the only nodes that should be considered. From positions and orientations throughout the target areas 80 and 81 as shown in FIG. 9, tool trajectories may be generated to reach from tube target locations and to the tool target location 70. Alternatively, the search may be further narrowed (saving computation time) by seeking nodes in a smaller spherical radius 79 as shown in FIG. 10.

As with the previous embodiment, the evaluation will involve a search from a candidate tube target location to a tube entry location within the free-space. The evaluation may be of a first node encountered having a lower heuristic cost, of all nodes with heuristic cost but within a given length of tool trajectory 77, or a fixed number of nodes having a heuristic value such that they are distributed over a specific length of tool trajectory 77. Computed tube-set alternatives may be displayed for a selection of one candidate as the final tube target location or alternatively, the final tube target location may be selected automatically based on the fewest number of component tubes generated during the searches.

Figure 11:
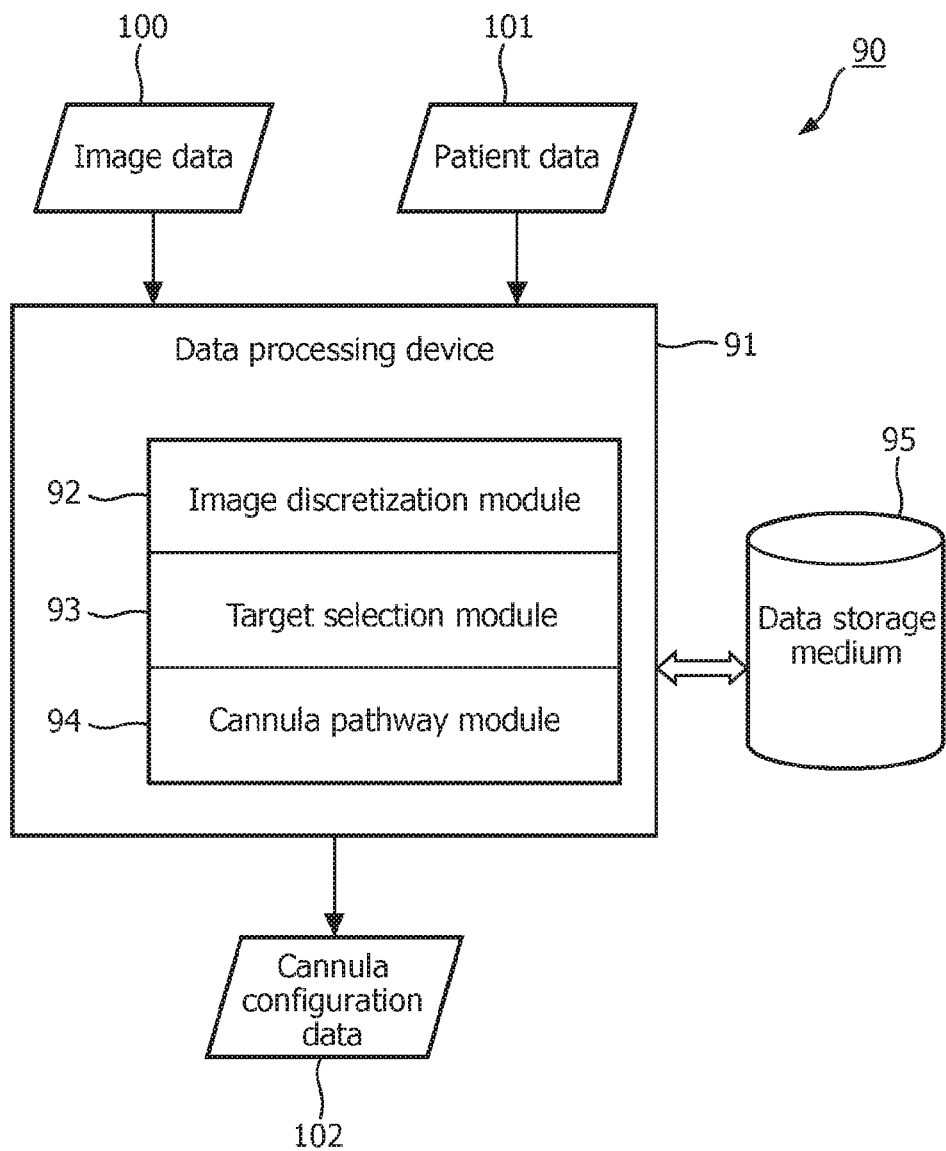
FIG. 11 illustrates a block diagram of a cannula configuration system in accordance with the present invention.

Referring to FIG. 11, a system 90 is illustrated for a cannula configuration application in accordance with the present invention. The system 90 includes a data processing device 91 and data storage medium 95. Data processing device 91 employs an image discretization module 92, a target selection module 93 and a cannula pathway module 94 for implementing the various inventive principles of the present invention as previously explained herein in connection with FIGS. 1-10. In general, image discretization module 92 performs all of the tasks necessary to construct a discretized configuration space node structure and the tube entry location within the data storage medium 95 as appropriate for the incoming image data 100 and patient data 101. Target selection module 93 performs all the tasks necessary selecting the tool target location, candidate tube target location(s) and the final tube target location. The cannula pathway module 94 performs all the tasks necessary for evaluating all of the candidate tube target location(s) via a propagation of cost waves as needed to fill the discretized configuration space node structure. The result is cannula configuration data 102 for specifying a configuration and dimensioning of a nested cannula between the target entry location and the tube target location.

In one embodiment, data 100-102 is processed locally as a pre-operative procedure. Alternatively, data 100-103 may be processed remotely (e.g., over the Internet) whereby a nested cannula may be assembled and shipped to the appropriate surgical site.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. A cannula configuration system, comprising:
an image discretization module operable to generate a discretized configuration space of a three dimensional image of an anatomical region, the discretized configuration space including a free-space for navigation of a nested cannula within the anatomical region and a forbidden space unreachable by the nested cannula;
a target selection module operable to select a tube target location within the free-space, the tube target location being derived from a computation of contiguous tool trajectory nodes of the discretized configuration space representative of a trajectory of a surgical tool extending through the nested cannula from the tube target location within the free-space to a tool target location within the forbidden space,
wherein a selection of the tube target location is a function of a heuristic cost metric of at least one tool trajectory node, each heuristic cost metric being indicative of an estimated distance from a corresponding tool trajectory node to a tube entry location into the free-space; and
a cannula pathway module operable to generate a series of concatenated path shapes between the tube entry location and the tube target location to form a cannula configuration pathway within the free-space, the cannula configuration pathway serving as a specification for configuring and dimensioning the nested cannula to reach the tube target location from the tube entry location.

2. The cannula configuration system of claim 1, wherein the selection of tube target location includes:
   an identification of a target area of the free-space; and
   a designation of at least one tool trajectory node within the target area of the free-space as a candidate tube target location.

3. The cannula configuration system of claim 2, wherein the target area is manually identified.

4. The cannula configuration system of claim 2, wherein the target area is automatically identified as a portion of the free-space within a sphere encircling the tool target location, the sphere having a radius as a function of the trajectory of the surgical tool.

5. The cannula configuration system of claim 4, wherein the radius of the sphere equals a length of the trajectory of the surgical tool.

6. The cannula configuration system of claim 4, wherein the radius of the sphere is less than a length of the trajectory of the surgical tool.

7. The cannula configuration system of claim 2, wherein the designation of at least one candidate tube target location includes:
   a search of at least one tool trajectory node having a non-infinite heuristic cost metric, the search starting at one end of the contiguous tool trajectory nodes; and
   a designation of a first tool trajectory node having the non-infinite heuristic cost metric encountered during the search as the candidate tube target location.

8. The cannula configuration system of claim 7, wherein the cannula configuration pathway is generated as a series of concatenated path shapes between the tube entry location and the first tool trajectory node to form the cannula configuration pathway within the free-space.

9. The cannula configuration system of claim 2, wherein the designation of at least one candidate tube target location includes:
   a search of at least one tool trajectory node having a non-infinite heuristic cost metric, the search starting at one end of the contiguous tool trajectory nodes; and
   a designation of a plurality of tool trajectory nodes during the search as candidate tube target locations, each designated tool trajectory node having the non-infinite heuristic cost metric.

10. The cannula configuration system of claim 9, wherein a number of candidate tube target locations equals a number of tool trajectory nodes within the free-space.

11. The cannula configuration system of claim 9, wherein a number of candidate tube target locations is less than a number of tool trajectory nodes within the free-space.

12. The cannula configuration system of claim 9, wherein a generation of the cannula configuration pathway includes:
   for each candidate tube target location, a generation of candidate series of concatenated path shapes between the tube entry location and the candidate tube target locations to form a candidate cannula pathway.

13. The cannula configuration system of claim 12, wherein the cannula configuration pathway is selected from among a plurality of candidate cannula pathways as a function of a number of concatenated path shapes within each candidate cannula pathway.

14. A system, comprising:
   a nested cannula configured and dimensioned to extend from a tube entry location into a free-space of a discretized configuration space of a three dimensional image of an anatomical region to a tube target location within the free-space; and
   a surgical tool configured and dimensioned to extend through the nested cannula from the tube target location to a tool target location within a forbidden space of the discretized configuration space,
      wherein the configuration of the nested cannula is derived from a computation of contiguous tool trajectory nodes of the discretized configuration space representative of a trajectory of the surgical tool from the tube target location through the free-space and the forbidden space to the tool target location, and
      wherein the configuration of the nested cannula is further derived from a selection of the tube target location as a function of a heuristic cost metric of at least one of the tool trajectory nodes within the free-space, each heuristic cost metric being indicative of an estimated distance from a corresponding tool trajectory node through the free-space space to a tube entry location into the free-space.

15. The cannula system of claim 14, wherein the nested cannula includes alternating curved and straight tubes.

16. A cannula configuration method, comprising:
   generating a discretized configuration space of a three dimensional image of an anatomical region, the discretized configuration space including a free-space for navigation of a nested cannula within the anatomical region and a forbidden space unreachable by the nested cannula;
   selecting a tube target location within the free-space, the tube target location being derived from a computation of a contiguous tool trajectory nodes of the discretized configuration space representative of a trajectory of a surgical tool extending through the nested cannula from the tube target location within the free-space to a tool target location within the forbidden space,
      wherein the tube target location is a function of a heuristic cost metric of at least one tool trajectory node, each heuristic cost metric being indicative of an estimate distance from a corresponding tool trajectory node to a tube entry location into the free-space; and
   generating a series of concatenated path shapes between the tube entry location and the tube target location to form a cannula configuration pathway within the free-space, the cannula configuration pathway serving as a specification for a configuration and dimensioning of the nested cannula to reach tube the tube target location from the tube entry location.

17. The cannula configuration method of claim 16, wherein the selection of the tube target location includes:
   identifying a target area of the free-space; and
   designating at least one tool trajectory node within the target area of the free-space as a candidate tube target location.

18. The cannula configuration method of claim 17,
   wherein the designation of at least one candidate tube target location includes:
      a search of at least one tool trajectory node having a non-infinite heuristic cost metric, the search starting at the tool target location; and
      a designation of a first tool trajectory node having the non-infinite heuristic cost metric encountered during the search as the candidate tube target location; and
   wherein the cannula configuration pathway is generated as a series of concatenated path shapes between the tube entry location and the first tool trajectory node to form the cannula configuration pathway within the free-space.

19. The cannula configuration method of claim 17, wherein the designation of at least one candidate tube target location includes:
 a search of at least one tool trajectory node having a non-infinite heuristic cost metric, the search starting at the tool target location; and
 a designation of a plurality of tool trajectory nodes during the search as candidate tube target locations, each designated tool trajectory node having the non-infinite heuristic cost metric; and
wherein a generation of the cannula configuration pathway includes: for each candidate tube target location, a generation of candidate series of concatenated path shapes between the tube entry location and the candidate tube target locations to form a candidate cannula pathway.

20. The cannula configuration method of claim 19, wherein the cannula configuration pathway is selected from among a plurality of candidate cannula pathways as a function of a number of concatenated path shapes within each candidate cannula pathway.

* * * * *